United States Patent [19]

David

[11] Patent Number: 5,638,811
[45] Date of Patent: Jun. 17, 1997

[54] ANATOMICAL INTRABUCCAL RESPIRATORY MOUTHPIECE

[76] Inventor: Michel David, 23 Rue Bony, 69004 Lyon, France

[21] Appl. No.: 612,892

[22] PCT Filed: Jul. 21, 1994

[86] PCT No.: PCT/FR94/00912

§ 371 Date: Mar. 7, 1996

§ 102(e) Date: Mar. 7, 1996

[87] PCT Pub. No.: WO96/03173

PCT Pub. Date: Feb. 8, 1996

[51] Int. Cl.⁶ ..................................................... A62B 7/00
[52] U.S. Cl. .................. 128/207.14; 128/206.29; 128/DIG. 26; 128/200.26
[58] Field of Search ................... 128/207.14, 207.15, 128/206.29, 200.26, DIG. 26, 912

[56] References Cited

U.S. PATENT DOCUMENTS

| | | |
|---|---|---|
| 3,107,667 | 10/1963 | Moore . |
| 4,136,689 | 2/1979 | Shamlian . |
| 4,495,945 | 1/1985 | Liegner . |
| 4,664,109 | 5/1987 | Rasocha .................. 128/207.14 |
| 4,715,368 | 12/1987 | George ..................... 128/136 |
| 4,862,903 | 9/1989 | Campbell ................. 128/206.29 |
| 4,901,737 | 2/1990 | Toone ...................... 128/848 |
| 5,031,611 | 7/1991 | Moles . |
| 5,062,422 | 11/1991 | Kinkade .................. 128/207.14 |

FOREIGN PATENT DOCUMENTS 699590 of 1953 United Kingdom .

OTHER PUBLICATIONS

Ferner H. & Staubesand J. 'Sobotta Atlas d'Anatomie Humaine' 1985, Urban & Schwarzenberg, DE, Munchne see FIG. 302.

*Primary Examiner*—Vincent Millin
*Assistant Examiner*—William J. Deane, Jr.
*Attorney, Agent, or Firm*—Harris Beach & Wilcox

[57] ABSTRACT

Anatomical intrabuccal respiratory mouthpiece in two parts, namely:

- a first extraoral part (1) having a first extrabuccal connection piece (2) intended to be joined to the gas source, and a second intrabuccal connection piece (5) whose outlet orifice is oblate (6);
- a second part (10) forming a flexible orthesis, associated with the intrabuccal connection piece (5), including:
  - vertical vestibules (11, 12) matching the anatomical shape of the vestibules, being the upper (11) and lower (12) vestibules, respectively;
  - upper (25) and lower (26) vertical lingual rims, respectively;
  - a plane interocclusal vestibulo-lingual pad (20) which joins the vestibules (11, 12) and the rims (25, 26) and is arranged horizontally at the junction between the upper and lower parts, the thickness of said plane pad (20) being slightly greater than that of the interocclusal gap of the jaws in the rest position;

characterized:

in that the oblate intrabuccal (5) outlet orifice (6) opens out within the thickness of the vestibulo-lingual pad (20);

and in that the upper vestibular part (11) arranged in the anteroposterior direction is situated in front of the lower vestibular part (12).

8 Claims, 3 Drawing Sheets

ANATOMICAL INTRABUCCAL RESPIRATORY MOUTHPIECE

TECHNICAL FIELD

The invention concerns an anatomical intrabuccal respiratory mouthpiece; it relates more particularly to an anatomical respiratory mouthpiece for medical usage, for example for patients "suffering from respiratory insufficiency", that is to say patients who can no longer spontaneously ventilate, permanently or temporarily, whatever the cause, such as patients suffering from myopathy, tuberculosis, or else for treatments, by medicinal or nonmedicinal aerosols, of contagious diseases (HIV positive, etc.). It also concerns a respiratory mouthpiece for skin diving.

In the rest of the description, the invention will be described more particularly in its medical application.

STATE OF THE ART

To assist ventilation in those with respiratory insufficiency, a flattened conical device is in most cases inserted into their mouths, said device having, at one end, a first circular extrabuccal connection piece intended to be joined to the source of oxygen-enriched air, and a second intrabuccal connection piece whose outlet orifice is oblate and has a slight rim so that it can be held by the patient's teeth. Although very widely used, this device has many disadvantages, namely, in particular:

lack of stability in the mouth, lack of tightness, inadvertent expulsions by the patient, especially during the night or during insufflation of air, said disadvantages necessitating an almost permanent monitoring of these patients.

To remedy these disadvantages, one might have considered equipping the intrabuccal end of this device with an appropriate orthesis. Unfortunately, this is not practicable, since the casting of the upper and lower maxillae, respectively, and mandibles, and the recording of the occlusion, are unfortunately not possible in view of the very serious condition of these patients.

Thus, despite the disadvantages mentioned hereinabove, the technique of the flattened device continues to be widely used.

In extreme cases, if this technique is not tolerated, or is rejected, it is necessary to proceed either with nasal intubations or with tracheotomy.

The document UK-A-699,950 describes a respiratory mouthpiece for patients who are to be subjected to electric shock treatment, said device including a molded part receiving the two jaws and intended to keep them apart. This device intended for a specific use (electric shocks) has a rigid tube which enters the mouth and covers a large part of the tongue, which causes considerable inconvenience. Moreover, it necessitates a mandibular overhang and cannot therefore be worn with comfort for a long period of time.

DESCRIPTION OF THE INVENTION

The invention overcomes these disadvantages. Its object is an intrabuccal respiratory device, in particular for patients requiring respiratory assistance, which is easy to manufacture, economical, does not have the disadvantages listed hereinabove, and can be put into place very easily, without having to take impressions or the like beforehand, irrespective of the condition or the configuration of the patient.

This anatomical intrabuccal respiratory mouthpiece which comprises two parts, namely:

a first extrabuccal part having a first extrabuccal connection piece intended to be joined to the gas source, and a second intrabuccal connection piece whose outlet orifice is oblate;

a second part forming a flexible orthesis, associated with the intrabuccal connection piece, including:

vertical vestibules matching the anatomical shape of the vestibules, being the upper and lower vestibules, respectively;

upper and lower vertical lingual rims, respectively;

a plane interocclusal vestibulo-lingual pad which joins the vestibules and the rims and is arranged horizontally at the junction between the upper and lower parts, the thickness of said plane pad being slightly greater than that of the interocclusal gap of the jaws in the rest position;

is characterized:

in that the oblate intrabuccal outlet orifice opens out within the thickness of the vestibulo-lingual pad;

and in that the upper vestibular part arranged in the anteroposterior direction is situated in front of the lower vestibular part.

In other words, in the case of a respiratory mouthpiece of the type in question, the invention consists, on the one hand, in providing a flexible orthesis with vertical vestibules and vertical lingual rims which are joined via a plane horizontal pad, and the implantation of the vestibules taking into consideration the average mandibular position in relation to the maxilla so as to avoid forward sliding of the mandible, and thereby to improve comfort, and, on the other hand, in ensuring that the oblate intrabuccal outlet orifice opens out into the plane pad so as not to cause any obstruction in the area of the tongue.

In this way, a standard device is afforded which is able to take account of the morphology of each patient and which can therefore be used immediately and effectively on any type of patient requiring respiratory assistance, irrespective of the cause.

Advantageously, in practice:

the oblate intrabuccal outlet orifice opens out in the front part or lateral parts, or even posterior parts, of the vestibulo-lingual pad;

the distance between the two upper and lower vestibular parts is of the order of two to four millimeters, advantageously in the region of three millimeters;

the thickness of the vertical vestibules decreases from the base, connecting with the pad, to their upper end; in one practical embodiment, the thickness of the vertical vestibules is approximately two millimeters at the base and one millimeter at the free end;

the free contour of the upper vestibule matches the contour of the bridles and frenula of the upper jaw; in this way, it is simple, with a pair of scissors, to modify this contour in the case where the vestibules are shallow or the frenula hypertrophic;

the thickness of the pads varies from three to four millimeters, and the width of the plane of the vestibulo-lingual portion is between ten and fifteen millimeters, depending on the model, in such a way as to be slightly greater than the thickness of the teeth; in this way, it is easy to make several models, in one of which the pads have a width of approximately ten millimeters, another with a mean width of twelve millimeters, and another with a width greater than fifteen millimeters;

the lingual rims have a thickness which diminishes gradually starting from the joining portion, for example from 2 to 1.5 mm;

the vestibules and the rims end substantially in the area of the second premolars;

the first extraoral part forms an angle of 15 to 30⁻, preferably in the region of 20⁻, in relation to the occlusion plane; this inclination has the advantage of ensuring that the pipe connecting the source of gas, for example air, to the extrabuccal connection piece does not point vertically upward when the patient is lying; thus, this pipe system is less vulnerable;

the orthesis is made of biocompatible and flexible thermoplastic material which is thermoformable, especially at the body temperature in the mouth area, in such a way that this intrabuccal orthesis adapts itself quickly and progressively to the actual buccal volume of the patient, or even rapidly by immersion in hot water (45° C.–50° C.); strongly plasticized, but uncharged, polyvinyl chloride (PVC) is used, for example, to achieve great pliability, or any other material having the same physical characteristics.

The manner in which the invention can be realized and the advantages which derive therefrom will become more apparent from the illustrative embodiment which follows, supported by the attached figures.

MANNER OF REALIZING THE INVENTION

Figure 1:
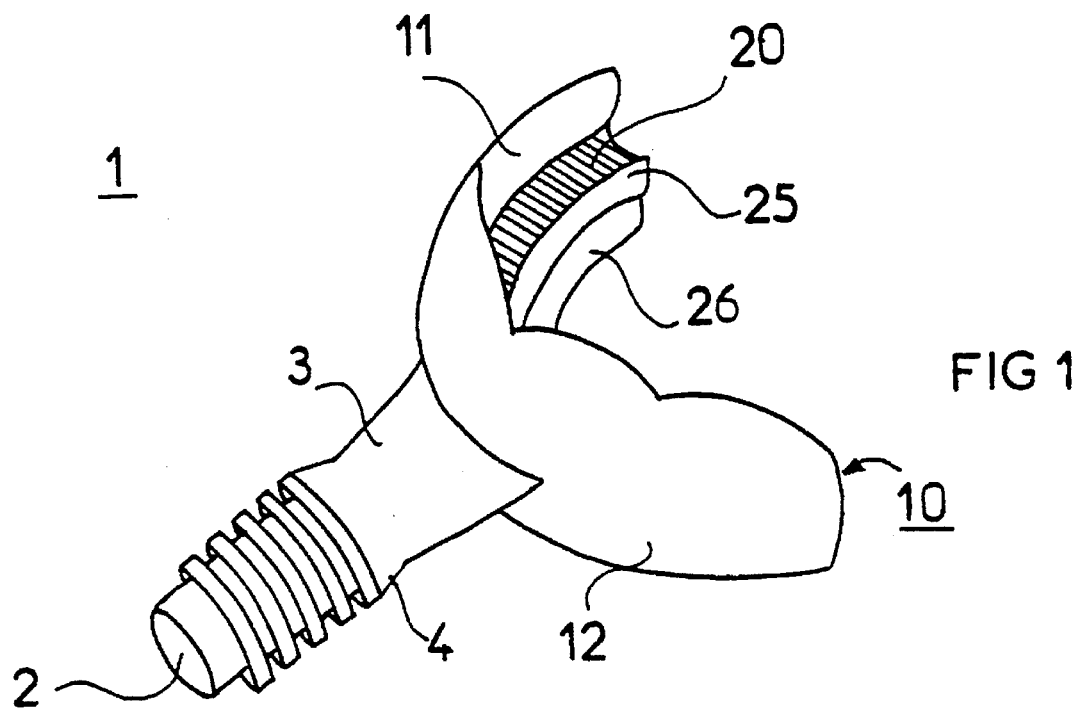
FIG. 1 is a general perspective representation, in a three-quarter view from the front, of a respiratory mouthpiece in accordance with the invention.
Figure 2:
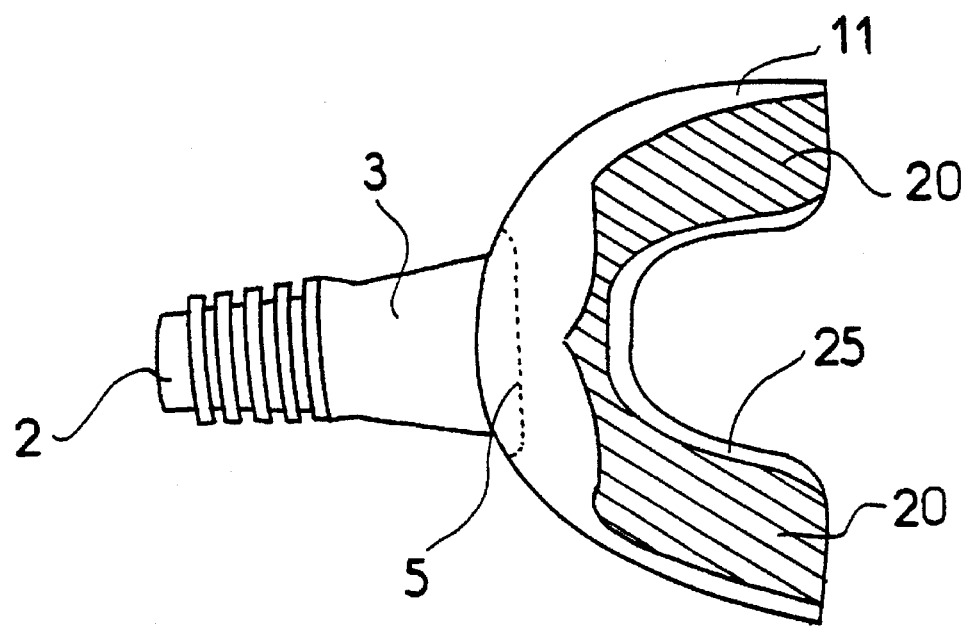
FIG. 2 is a plan view of this mouthpiece, in horizontal longitudinal section in FIG. 3.
Figure 3:
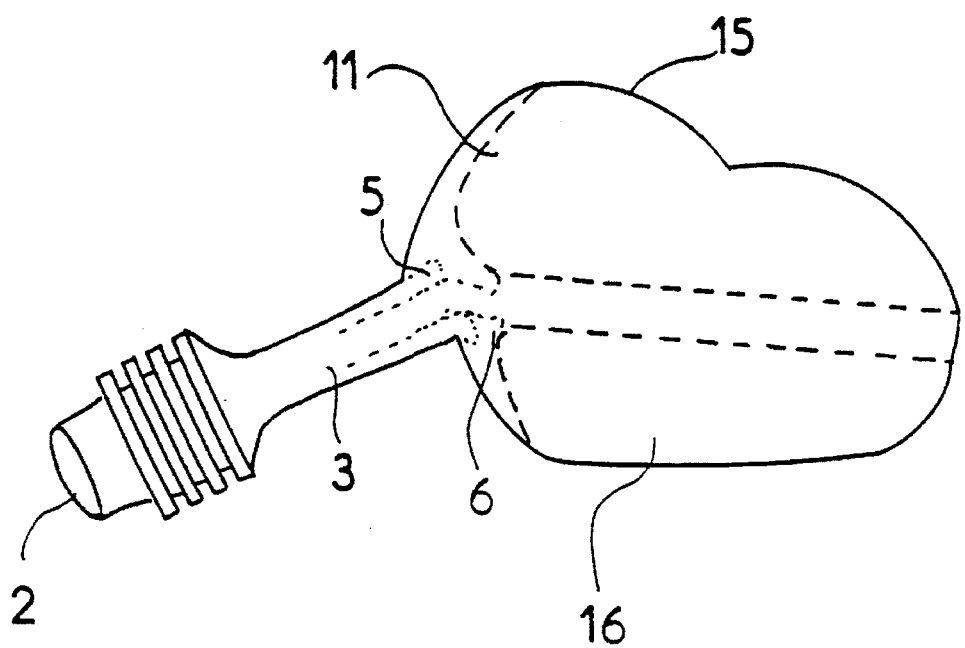
FIG. 3 is a horizontal section of FIG. 2.

Referring to the figures, the anatomical intrabuccal respiratory mouthpiece in accordance with the invention essentially comprises two parts which are made integral with each other, for example cast en bloc or heat-sealed, namely a first part designated by the general reference (1) and a second part designated by the general reference (10), respectively. It goes without saying that these two main parts can themselves be made up of a number of secondary parts.

The first extraoral part (1), which is known in other respects, and which, corresponding to the prior art, comprises a first extrabuccal cylindrical connection piece (2) intended to be joined to the source of gas, for example oxygen-enriched air, then a body (3) in the shape of a flattened truncated pyramid joined to the connection piece (2) via a truncated portion (4). This body (3) finishes in a second intrabuccal connection piece (5) whose outlet orifice (6) is oblate, for example has a rectangular cross section of twenty millimeters by two millimeters.

The first part of the mouthpiece (1) is associated with a second part (10) forming a flexible orthesis, for example made of strongly plasticized PVC. This second part (10) in the first instance comprises two vertical vestibules, upper (11) and lower (12), respectively, whose shape matches the anatomical shape of the vestibules.

In one practical embodiment, the base (13, 14) connecting these vestibules (11, 12) to the intrabuccal outlet orifice (5, 6) has a thickness near to two millimeters, whereas the free end (15, 16) has a thickness near to one millimeter.

The second part (10) also includes, arranged horizontally at the junction of the upper (11) and lower (12) parts, a plane vestibulo-lingual pad designated by the reference (20) in the shape of a smooth or even striated interocclusal horizontal platform joining the vestibules (11, 12) to the upper rim (25) and lower rim (26), respectively, of the two substantially vertical lingual rims (25, 26).

According to another important characteristic of the invention, the thickness of the horizontal plane pads (20) is slightly greater than the interocclusal gap between the jaws in the rest position, which allows for a good hold in the mouth, without any strain and without muscle contraction, the teeth resting on the pads (20).

Figure 4:
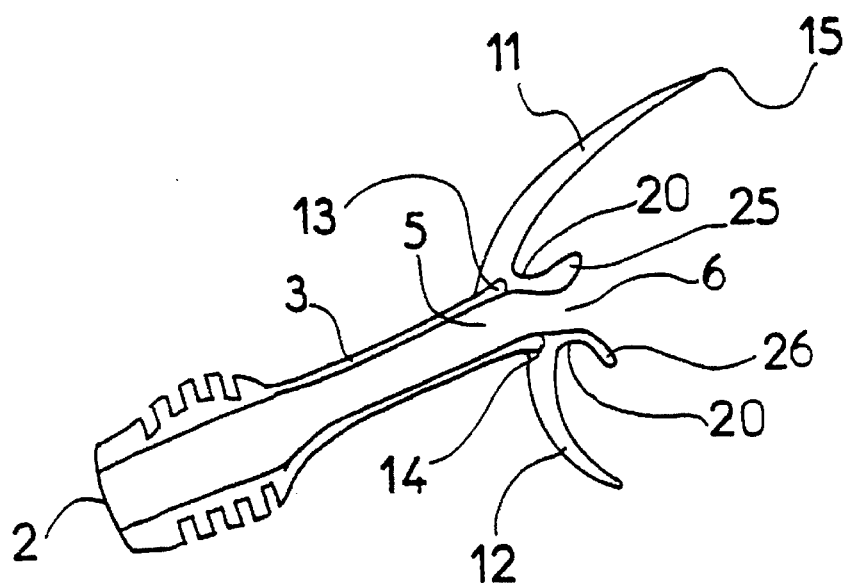
FIG. 4 is a detailed view of the connection of the first extraoral part to the second part.

Likewise, according to one important characteristic of the invention, the oblate (6) intrabuccal (5) outlet orifice opens out within the thickness of the vestibulo-lingual pad (20) (see FIG. 4).

In one variant, the mouthpiece of the invention can also be used in cases of substantial prognathism by reversing it and cutting it appropriately.

It can also be used in an emergency situation in order to provoke the protrusion of the mandible in such a way as to free the airways.

Figure 5:
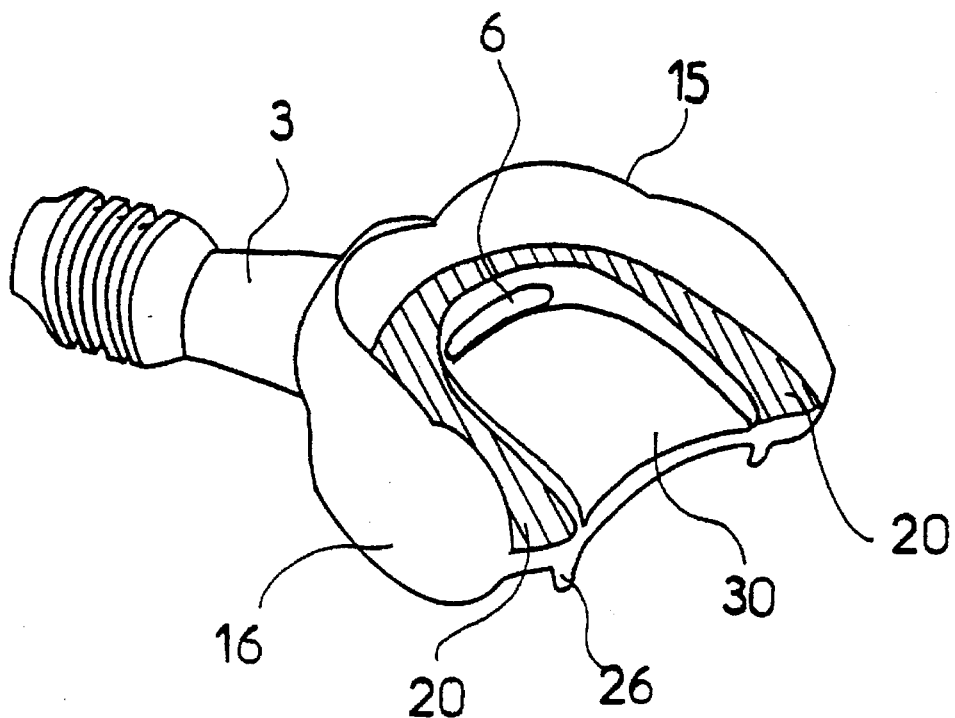
FIG. 5 is a general perspective representation, in a three-quarter view from the rear, of another embodiment of the invention, shown in a rear view in FIG. 6.
Figure 6:
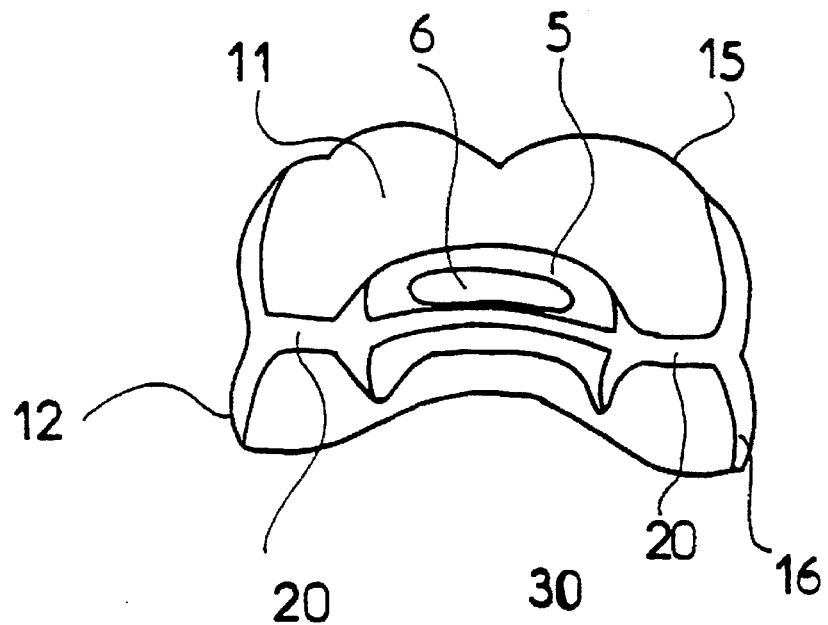
FIG. 6 is a rearview of FIG. 5.

In another variant, which is shown in FIG. 5, the intraocclusal pads (20) are connected to each other by a small, horizontal and slightly curved flap (30) intended to immobilize the tongue so as to avoid the risk of obturating the buccopharyngeal orifice.

The device according to the invention has many advantages compared to those marketed at present and cited in the preamble. The following may be mentioned:

the possibility of making a limited number of models by virtue of a standard device, for example small, medium and large models, or even neonatal models, without having to take impressions, which, as is known, are impossible to obtain from these patients;

the possibility of having at one's disposal devices which can be used immediately, in particular in patients suffering attacks;

inherent adaptability to the buccal volume of the patient;

good stability in the mouth, avoiding accidental loss, particularly during sleep or during a coma;

excellent tightness;

no inadvertent expulsion;

the fact that the patient does not have to make any effort to keep the device in the mouth;

the ease with which the contour can be modified in order to adapt better to the morphology of the patient.

In this way, this device can be used successfully for all types of medical respiratory insufficiency, particularly when a disposable device is sought.

It can also be used on completely or partially edentulous patients.

This device can also be used successfully for mouthpieces for skindiving, since it prevents forward sliding of the mandible, which in the long term generates pain in the temporomandibular joint. In this application, the extraoral part (1) can be connected directly to the pressure regulator or to the surface breathing tube, commonly called "snorkel".

I claim:

1. An anatomical intrabuccal respiratory mouthpiece in two sections that includes:

a first extraoral section having an extrabuccal connection piece that is connectable to a gas source and an intrabuccal connection piece having an oblate outlet orifice, a second section forming a flexible orthesis associated with said intrabuccal connection, said second section further including:

two vertical vestibules matching an anatomical shape of the vestibules, said vertical vestibules consisting of an upper and a lower vestibule, upper and lower vertical lingual rims, and an interocclusal vestibulo-lingual plane pad which joins the vestibules and the rims and is arranged horizontally at a junction between the upper and lower vestibules, a thickness of said vestibulo-lingual plane pad being slightly greater than that of an interocclusal gap of upper and lower jaws therein when said jaws are in a rest position, said second section is made of biocompatible and flexible thermoplastic material which is thermoformable at standard body temperature in a mouth area;

said outlet orifice of said intrabuccal connection piece opens outwardly within the thickness of the vestibulo-lingual plane pad, and said upper vestibule being arranged in an antero-posterior direction is situated in front of the lower vestibule.

2. Respiratory mouthpiece according to claim 1, wherein the oblate outlet orifice opens out at a front, or in a lateral or posterior part, of the vestibulo-lingual plane pad.

3. Respiratory mouthpiece according to claim 2, wherein a distance between the upper and lower vestibules is between two and four millimeters.

4. Respiratory mouthpiece according to claim 3, wherein a thickness of the vestibules decreases from a base, connected with the pad, toward an opposite end thereof.

5. Respiratory mouthpiece according to claim 4 wherein the upper vestibule has a free contour that matches a contour of bridles and frenula of the upper jaw.

6. Respiratory mouthpiece according to claim 5 wherein the thickness of the horizontal vestibulo-lingual pad is between three and four millimeters, and a width of the pad is between ten and fifteen millimeters.

7. Respiratory mouthpiece according to claim 6, the first extraoral section forms an angle of 15° to 30° in relation to an occlusion plane.

8. Respiratory mouthpiece according to claim 7 wherein the second section is made of biocompatible and flexible thermoplastic material which is thermoformable at the body temperature in the mouth area.

* * * * *